United States Patent

Hain et al.

(10) Patent No.: US 8,196,473 B2
(45) Date of Patent: Jun. 12, 2012

(54) METHOD FOR SYNCHRONIZATION OF ULTRASONIC TRANSDUCERS IN A MOVEMENT SYSTEM

(75) Inventors: Stefan Hain, Effeltrich (DE); Hubert Mooshofer, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 482 days.

(21) Appl. No.: 12/407,140

(22) Filed: Mar. 19, 2009

(65) Prior Publication Data

US 2009/0320602 A1    Dec. 31, 2009

(30) Foreign Application Priority Data

Mar. 20, 2008  (DE) .......................... 10 2008 015 236
Jan. 19, 2009  (DE) .......................... 10 2009 005 112

(51) Int. Cl.
| | |
|---|---|
| G01N 29/00 | (2006.01) |
| G01N 29/04 | (2006.01) |
| G01N 9/24 | (2006.01) |
| G01R 33/20 | (2006.01) |
| H02K 33/00 | (2006.01) |
| H02P 1/00 | (2006.01) |
| H02P 3/00 | (2006.01) |
| H02P 5/00 | (2006.01) |
| H02P 7/00 | (2006.01) |

(52) U.S. Cl. ............... 73/632; 73/618; 73/619; 318/128

(58) Field of Classification Search .................. 73/1.46, 73/1.48, 618, 634, 641, 620, 627, 629, 623
See application file for complete search history.

(56) References Cited

U.S. PATENT DOCUMENTS

| | | | | |
|---|---|---|---|---|
| 4,213,183 | A | * | 7/1980 | Barron et al. .................... 702/39 |
| 4,980,865 | A |   | 12/1990 | Ishibashi et al. ................ 367/11 |
| 5,239,515 | A | * | 8/1993 | Borenstein et al. ............. 367/87 |

FOREIGN PATENT DOCUMENTS

| | | |
|---|---|---|
| DE | EP0892492 A1 * | 1/1999 |
| DE | 10014936 C1 | 10/2001 |
| EP | 0892492 A1 | 1/1999 |

OTHER PUBLICATIONS

Patent and Machine Translation of EP0892492-A1, Date Translated: Oct. 21, 2011, Publisher: European Patent Office, Espacenet Patent Search.*

* cited by examiner

*Primary Examiner* — Lisa Caputo
*Assistant Examiner* — Roger Hernandez-Prewitt
(74) *Attorney, Agent, or Firm* — King & Spalding L.L.P.

(57) ABSTRACT

In a device and method for non-destructive materials testing with at least one ultrasonic transducer, the transducer is able to be moved by a movement system in at least one direction to a workpiece surface. The emission of ultrasonic by the ultrasonic transducer is able to be synchronized with the activation of the movement system so that electrical interference caused by the movement system occurs at times at which no echo is expected for ultrasonic emitted by the transducer. The method and device can be applied to non-destructive materials testing with ultrasound.

12 Claims, 4 Drawing Sheets

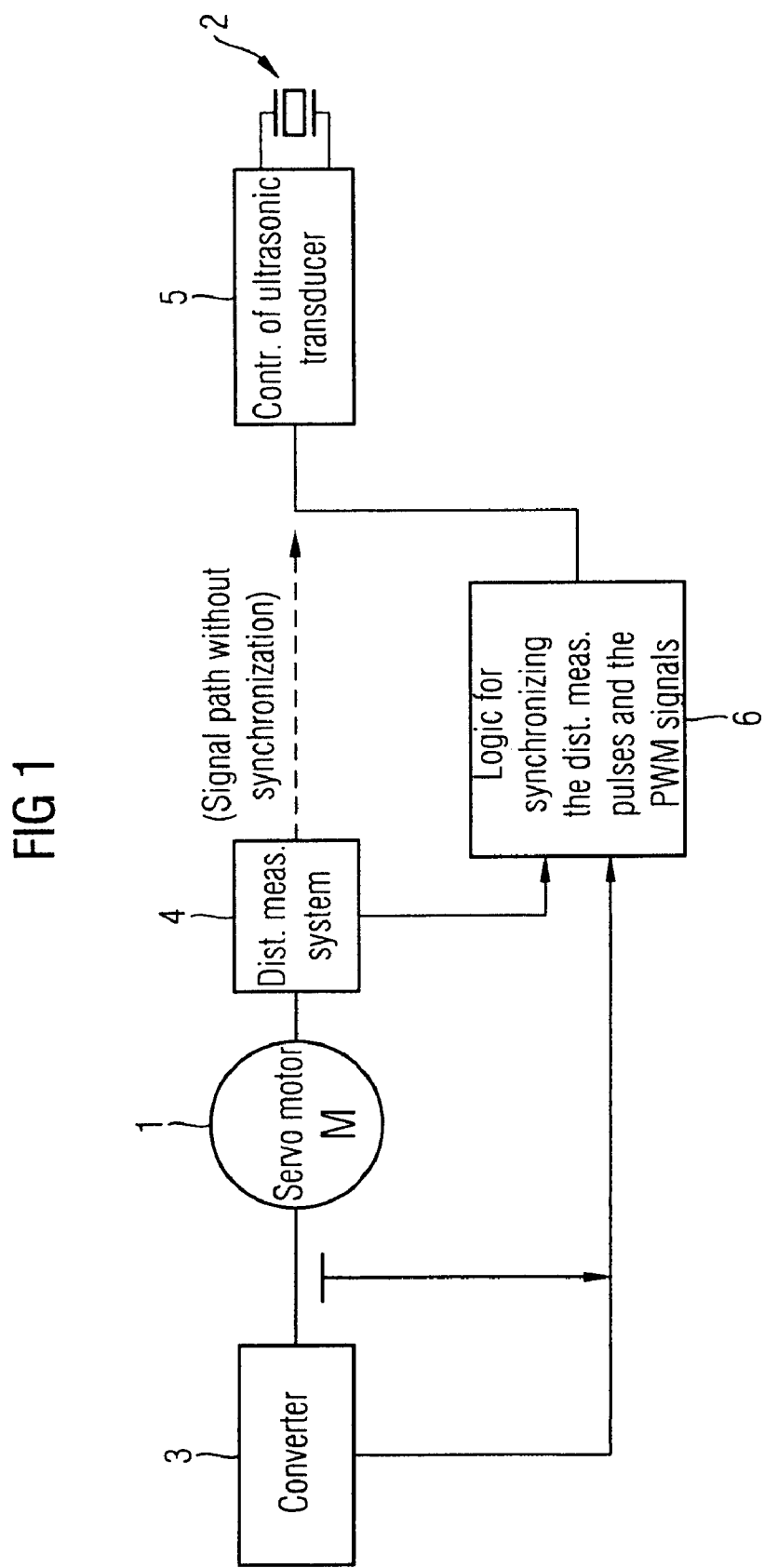

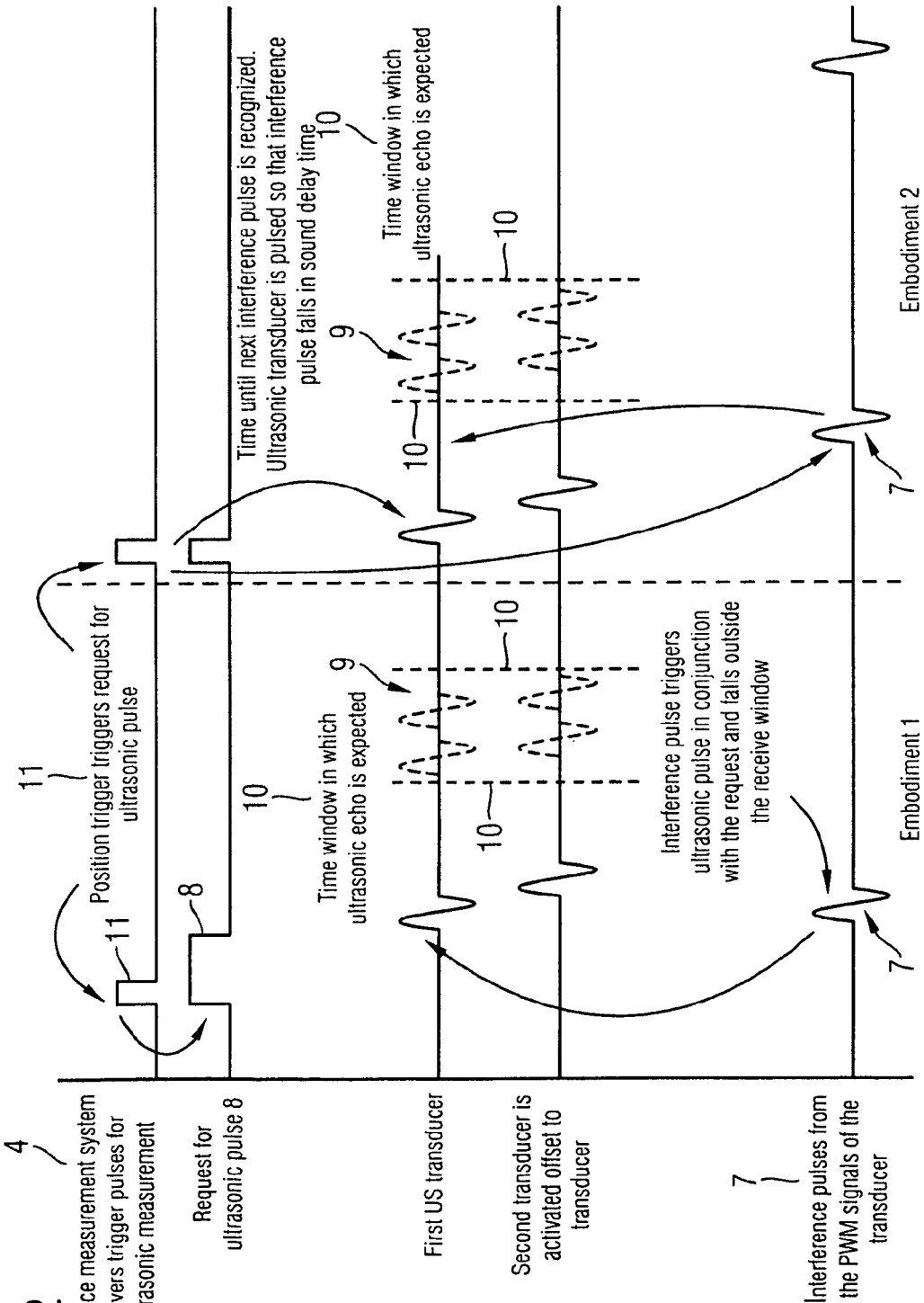

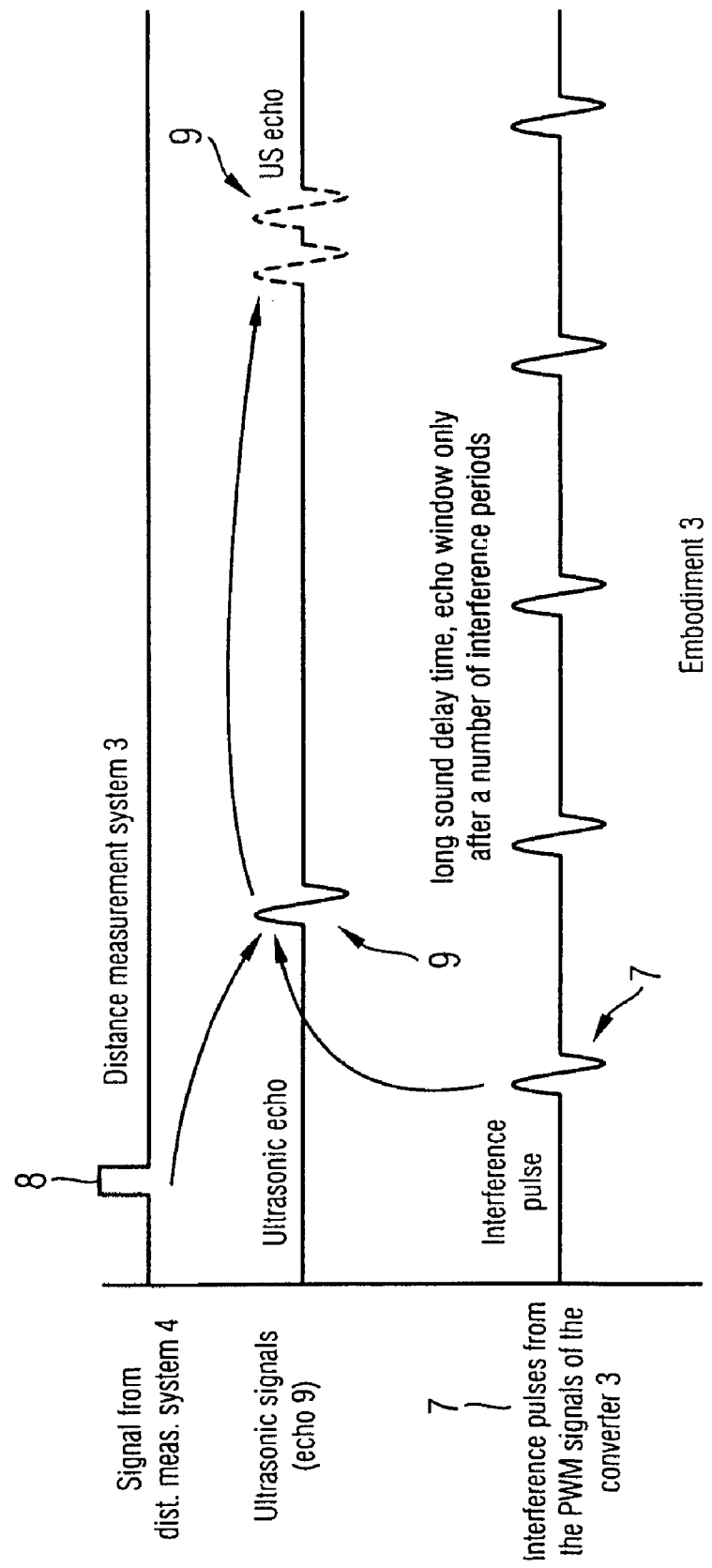

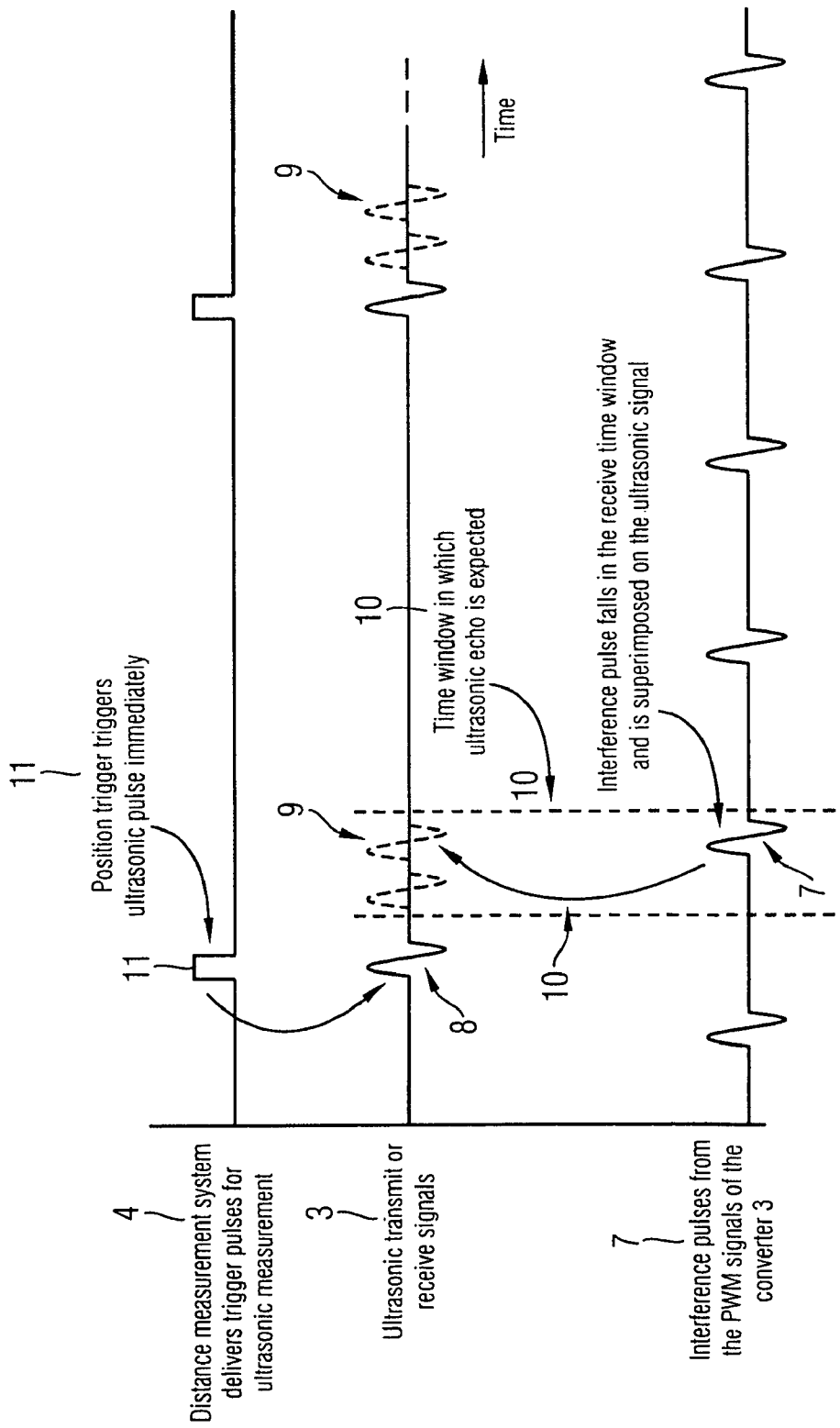

METHOD FOR SYNCHRONIZATION OF ULTRASONIC TRANSDUCERS IN A MOVEMENT SYSTEM

CROSS-REFERENCE TO RELATED APPLICATIONS

This application claims priority to German patent application No. 10 2008 015 236.6, filed Mar. 20, 2008 and German patent application No. 10 2009 005 112.0, filed Jan. 19, 2009. The complete disclosure of the above-identified priority applications is hereby fully incorporated herein by reference.

TECHNICAL FIELD

The invention relates to non-destructive materials testing with at least one ultrasonic transducer which is able to be conveyed in a movement system relative to a workpiece, with ultrasonic pulses being emitted and echo signals being received.

BACKGROUND

A normal procedure for non-destructive materials testing with ultrasound (US) consists of one or more ultrasonic transducers being moved past the contour of a test object, whereby a map of the test object is created with any faults that may have been found.

Ultrasonic transducers in such cases are located in a positioning system which is usually moved by servo motors. Their operating currents are adjusted by converters using pulse width modulation (PWM). The destination points for outputting the pulses and the evaluation of the incoming echoes are controlled by the positioning system in order to obtain the assignment of the signals to the measurement location.

While the signal voltage of the ultrasonic transducer, triggered by the ultrasonic echo only amounts to a few mV, the operating voltages and currents of the servomotors can amount to a few hundred volts and a few amperes. The pulse width modulation of these voltages and currents produces steep switching edges on the motor lines, which can couple into the signal circuit of ultrasonic transducers by electromagnetic coupling. Thus undesired interference voltages of the same order of magnitude as the desired signal voltages can be generated and the measurement result corrupted by said interference. This situation can be seen in FIG. 4.

To find material faults with a different orientation to the surface, one and the same point on the surface is tested frequently by different ultrasonic transducers with different angles of incidence. The sequential activation of the individual transducers significantly lengthens the testing time.

SUMMARY

According to various embodiments, a device for separating useful ultrasonic signals from interference signals from movement systems can be provided.

According to an embodiment, in a device for non-destructive materials testing with at least one ultrasonic transducer, the transducer is able to be moved by a movement system in at least one direction towards the workpiece surface, and the emission of ultrasound by means of the ultrasonic transducer is able to be synchronized with the control of the movement system such that electrical interference by the movement system occurs at times at which the ultrasound sent out by the transducer does not expect an echo.

According to a further embodiment, a number of ultrasonic transducers which transmit sound to one point from different directions may be able to be controlled in a nested manner over time by one scheduling unit.

According to another embodiment, in a method for non-destructive materials testing, ultrasound may be emitted with at least one ultrasonic transducer, the transducer may be moved continuously or in steps by means of a movement system, and the emission of ultrasound by means of the ultrasonic transducer can be synchronized with the control of the movement system such that electrical interference by the linear movement system occurs during the times at which no echo is expected for the ultrasound sent out by the transducer.

According to a further embodiment, an ultrasonic pulse can be emitted before the occurrence of an interference pulse by the movement system such that the echo of the ultrasonic pulse arrives at the transducer after the interference pulse. According to a further embodiment, a time delay of the ultrasonic pulses generated by synchronization, which can produce a corresponding local uncertainty of the measurement in respect of the positioning system relative to the workpiece surface, can be ignored for usual speeds of movement and PWM frequencies. According to a further embodiment, for a known repetition frequency of the PWM interference pulses the method may be controlled by the interference pulses occurring when the ultrasonic pulses are underway but no echo is expected yet. According to a further embodiment, for a known repetition frequency of the PWM interference pulses a time window for echo signals, taking into account a number of interference periods, can be placed in the interference-free time.

BRIEF DESCRIPTION OF THE DRAWINGS

Exemplary embodiments are described below with reference to the accompanying schematic figures.

FIG. 1 shows a circuit with converter 3, motor 1, distance measurement system 4, synchronization 6 and ultrasonic transducer 2, FIG. 2 shows two embodiments to depict different signals with different transmit and receive times, FIG. 3 shows an embodiment in which a number of interference periods are taken into account, FIG. 4 shows the previous timing circumstances without synchronization.

DETAILED DESCRIPTION

In accordance with various embodiments the times at which the ultrasonic transducers emit pulses and then wait for the US echo are not directly or exclusively determined by the distance measurement system of a positioning device, but additionally synchronized relative to the switch edges of the pulse width modulation/PWM signals of motor supply lines. Thus echo signals of the ultrasound system do not arrive at the same time as coupled-in PWM signals which represent interference signals for the ultrasonic echo signals.

Pulses necessary for this can either be derived directly from converters or for example, if such converters are not accessible, also decoupled capacitively or inductively from the motor leads.

A synchronizing logic and scheduling unit now evaluates the pulses of the path measuring system and the PWM signal and controls the ultrasonic transducer by logical operations and delays such that the expected ultrasonic echo is expected at a time in which no PWM interference pulses arise.

FIG. 1 shows a switching scheme, with ultrasonic transducers 2 being controlled by a control 5 and integrated into a movement system for scanning a specific material surface, in that they are moved by motors 1, with a distance measurement system 4 controlling this movement. Based on known systems, control signals, which are created exclusively by the distance measurement system 4, are replaced by a combined control based on the signals of the distance measurement system 4 and additionally on the switching edges of the pulse width modulation signals, which appear in the motor supply lines.

FIG. 4 shows a signal organization which is associated in accordance with the previous state of development with the interference influence of the pulse width modulation signals on the ultrasonic echo signals. FIG. 4 shows three different signals at three corresponding levels, with the development over time extending to the right. A signal which is referred to as a position trigger 11 is shown in the upper signal path. The distance measurement system 4 delivers trigger pulses for the ultrasonic measurement. This gives an assignment between a predetermined location on a workpiece surface and a measurement. In accordance with the position trigger 11 ultrasonic transmit signals 8 are sent out. Reflected ultrasonic echo signals 9 are expected at specific times and arrive at the ultrasonic transducer after their reflection on the workpiece surface.

The signal path shown at the bottom in FIG. 4 shows the interference pulses 7 corresponding to the pulse width modulation signals of the converter 3. If the time window 10, which is shown by broken lines on two sides, is used for orientation, it can be established that an interference pulse 7 arrives at the same time as the ultrasonic echo pulses 9, which leads to significant disruption of the ultrasonic receiving system. Since the time window outlines the period in which ultrasonic echoes 9 are expected, this time window 10 is used as an orientation aid for further considerations.

The time delay of the ultrasonic pulses arising through the synchronization according to various embodiments and thus the associated positional uncertainty of the measurement in respect of the positioning system relative to the workpiece surface can be ignored for the speeds of movement and PWM frequencies which usually occur.

FIG. 2 shows the following on a total of five signal paths: From top to bottom, the first path shows the position trigger 11 of the distance measurement systems 4, which in the second level from the top shows a request for an ultrasonic pulse 8. At the third level from the top interference signals 7 and ultrasonic echo signals 9 to be observed at a first ultrasonic transducer 1 are shown. At the fourth level from the top the signals of a further ultrasonic transducer which is activated with a time offset from the first ultrasonic transducer are outlined. The lowest level shows the interference pulses 7 with the pulse width modulation signals of the converter.

FIG. 2 overall shows the signal organization of two ultrasonic transducers 2 which are controlled offset in time. The left part of FIG. 2 shows the embodiment in which ultrasonic transducers send out signals at short intervals. These arrive back as echoes shortly after one another at the ultrasonic transducers and can be recorded separately.

In FIG. 2 a position trigger 11 is not flagged with an ultrasonic pulse 8 separately for each ultrasonic transducer. Starting from the interference signals 7, which appear offset in time between the first and second ultrasonic transducer, the ultrasonic echo signals 9 arrive offset in time in the corresponding time window 10. This solution is associated with the fact that the scheduling unit is used to control a number of ultrasonic transducers nested in time.

The embodiment 2 shown in FIG. 2 in the right half of the figure is based on a known repetition frequency of the pulse width modulation signals. In this case a number of time windows 10 are observed for echo signals 9, with a number of interference periods being present one after the other. Taking into account a number of interference periods and with a known frequency of the interference signals, this determination makes possible an interference-free time in which the ultrasonic echo signals 9 can occur explicitly or can be expected in time windows 10.

A third embodiment is shown in FIG. 3, with once again, for a known frequency of the interference signals, the echo signals to be expected being placed in interference-free times taking into account a number of interference periods. The special feature of this embodiment lies in the inclusion of a long sound delay time, with a window for ultrasonic echo signals 9 only being generated after a number of interference periods.

In addition the scheduling unit can be used to control a number of ultrasonic transducers which emit sound from several directions towards a point, so that they are nested in time. The transducers then transmit ultrasonic pulses at short intervals. These are underway simultaneously for some time and arrive as echo back at the transducers shortly after one another and can be recorded separately; see FIG. 2, embodiment 1.

When the repetition frequency of the PWM interference pulses is known, the control can also be undertaken so that the interference pulses arrive when the ultrasonic pulses are underway but no echo is yet expected; see FIG. 2, embodiment 2.

If the frequency of the interference signals is known, a time window for echo signals taking into account a number of interference periods be relocated onwards into the interference-free time; see FIG. 3, embodiment 3.

By masking out the interference pulses from the expected echo signal the sensitivity of the fault detection can be significantly improved and makes it possible in the individual case to distinguish between interference pulse and fault echo for the first time. The outlay for the signal processing and screening measures can be reduced. The nesting ultrasonic transducer control reduces the testing time. The control of the transducers can be simplified by transmit and receive channels being used multiple times. For synchronization of control on a known PWM frequency the measurement location can be better adapted to the ideal grid in respect of position and movement and measurements can also be conducted for long sound delay times by comparison with the PWM period duration.

What is claimed is:

1. A method for non-destructive materials testing, comprising the steps of: emitting ultrasound with at least one ultrasonic transducer, moving the transducer continuously or in steps by means of a movement system, synchronizing the emission of ultrasound by means of the ultrasonic transducer with the control of the movement system such that electrical interference by the linear movement system occurs during the times at which no echo is expected for the ultrasound sent out by the transducer, wherein an ultrasonic pulse is emitted before the occurrence of an interference pulse by the movement system such that the echo of the ultrasonic pulse arrives at the transducer after the interference pulse.

2. The method according to claim 1, wherein for usual speeds of movement and PWM frequencies a time delay of the ultrasonic pulses generated by synchronization is ignored, wherein the time delay can produce a corresponding local uncertainty of the measurement with respect of the positioning system relative to the workpiece surface.

3. The method according to claim 1, wherein, for a known repetition frequency of PWM interference pulses, controlling an interference pulse such that the interference pulse occurs when a ultrasonic pulse is underway but no echo is expected yet.

4. The method according to claim 1, comprising the steps of placing, for a known repetition frequency of the PWM interference pulses, a time window for echo signals, taking into account a number of interference periods, in the interference-free time.

5. A method for non-destructive materials testing, comprising the steps of: emitting ultrasound with at least one ultrasonic transducer, moving the transducer continuously or in steps by means of a movement system, synchronizing the emission of ultrasound by means of the ultrasonic transducer with the control of the movement system such that electrical interference by the linear movement system occurs during the times at which no echo is expected for the ultrasound sent out by the transducer wherein for usual speeds of movement and PWM frequencies a time delay of the ultrasonic pulses generated by synchronization is ignored, wherein the time delay can produce a corresponding local uncertainty of the measurement in respect of the positioning system relative to the workpiece surface.

6. The method according to claim 5, wherein an ultrasonic pulse is emitted before the occurrence of an interference pulse by the movement system such that the echo of the ultrasonic pulse arrives at the transducer after the interference pulse.

7. The method according to claim 5, wherein, for a known repetition frequency of PWM interference pulses, controlling an interference pulse such that the interference pulse occurs when a ultrasonic pulse is underway but no echo is expected yet.

8. The method according to claim 5, comprising the steps of placing, for a known repetition frequency of the PWM interference pulses, a time window for echo signals, taking into account a number of interference periods, in the interference-free time.

9. A method for non-destructive materials testing, comprising the steps of: emitting ultrasound with at least one ultrasonic transducer, moving the transducer continuously or in steps by means of a movement system, synchronizing the emission of ultrasound by means of the ultrasonic transducer with the control of the movement system such that electrical interference by the linear movement system occurs during the times at which no echo is expected for the ultrasound sent out by the transducer, wherein, for a known repetition frequency of PWM interference pulses, an interference pulse is controlled such that the interference pulse occurs when a ultrasonic pulse is underway but no echo is expected yet.

10. The method according to claim 9, wherein an ultrasonic pulse is emitted before the occurrence of an interference pulse by the movement system such that the echo of the ultrasonic pulse arrives at the transducer after the interference pulse.

11. The method according to claim 9, wherein for usual speeds of movement and PWM frequencies a time delay of the ultrasonic pulses generated by synchronization is ignored, wherein the time delay can produce a corresponding local uncertainty of the measurement with respect of the positioning system relative to the workpiece surface.

12. The method according to claim 9, comprising the steps of placing, for a known repetition frequency of the PWM interference pulses, a time window for echo signals, taking into account a number of interference periods, in the interference-free time.

\* \* \* \* \*